United States Patent [19]

Malick

[11] 4,303,884

[45] Dec. 1, 1981

[54] INFLATABLE EDDY CURRENT INSPECTION PROBE FOR INSPECTION OF TUBULAR MEANS

[75] Inventor: Franklin S. Malick, Monroeville, Pa.

[73] Assignee: Westinghouse Electric Corp., Pittsburgh, Pa.

[21] Appl. No.: 952,889

[22] Filed: Oct. 19, 1978

[51] Int. Cl.³ .................. G01N 27/72; G01N 27/82; G01R 33/12
[52] U.S. Cl. .................................................. 324/220
[58] Field of Search ............................. 324/219–221

[56] References Cited

U.S. PATENT DOCUMENTS

| | | |
|---|---|---|
| 1,583,208 | 10/1927 | Walker et al. |
| 2,451,600 | 10/1948 | Woodcock . |
| 2,622,125 | 12/1952 | Bender .................................. 324/220 |
| 2,876,413 | 12/1952 | Saurenman et al. . |
| 2,994,962 | 8/1961 | LeBourg . |
| 3,024,651 | 3/1962 | McGlasson . |
| 3,097,433 | 7/1963 | Cubberly . |
| 3,251,134 | 5/1966 | Wojcik . |
| 3,488,856 | 1/1970 | Wiklund . |
| 3,543,144 | 11/1970 | Walters et al. ..................... 324/221 |
| 3,914,870 | 10/1975 | Wiedenmann . |
| 3,940,689 | 2/1976 | Johnson, Jr. ......................... 324/221 |
| 4,050,384 | 9/1977 | Chapman . |
| 4,063,157 | 12/1977 | Lorenzi et al. ..................... 324/220 |
| 4,153,875 | 5/1979 | Pigeon et al. ...................... 324/220 |

Primary Examiner—Gerard R. Strecker
Assistant Examiner—Walter E. Snow
Attorney, Agent, or Firm—L. A. DePaul; Z. L. Dermer

[57] ABSTRACT

The inspection probe for inspecting tubular members comprises a plurality of axially oriented plastic strips which form the circumference of the probe with each plastic strip having mounted thereon an eddy current coil. A rubber tube is disposed on the interior of the plastic strips so that when the rubber tube is inflated, the plastic strips and coils are forced outward into close contact with the tubular member so that the eddy current coils can detect flaws in the tubular member. The eddy current coils are held against the tube wall even when the tube has been deformed into an irregular configuration.

6 Claims, 7 Drawing Figures

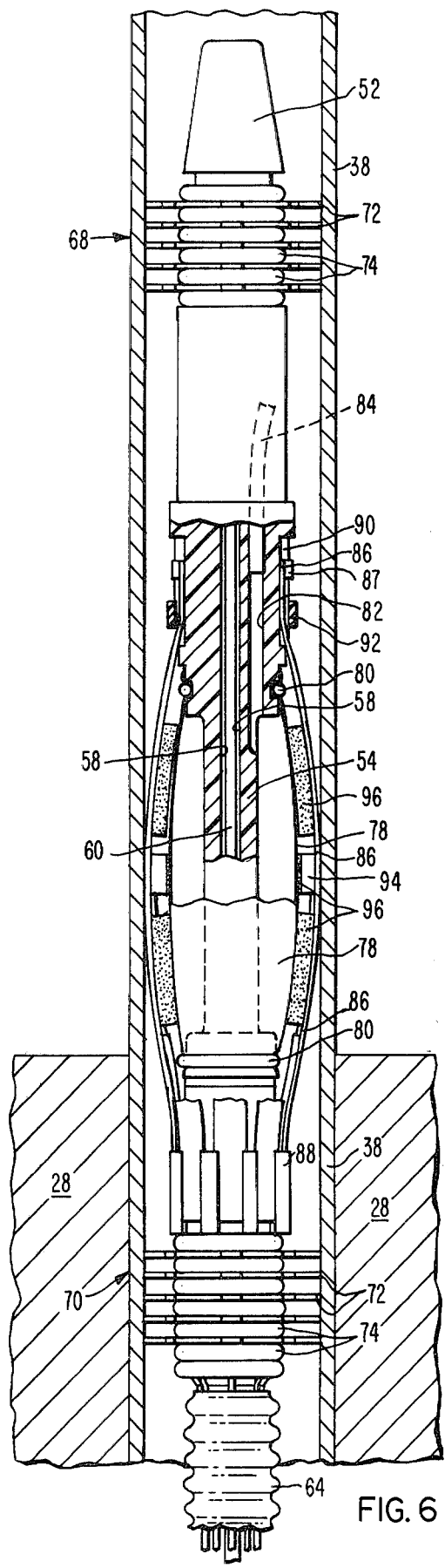
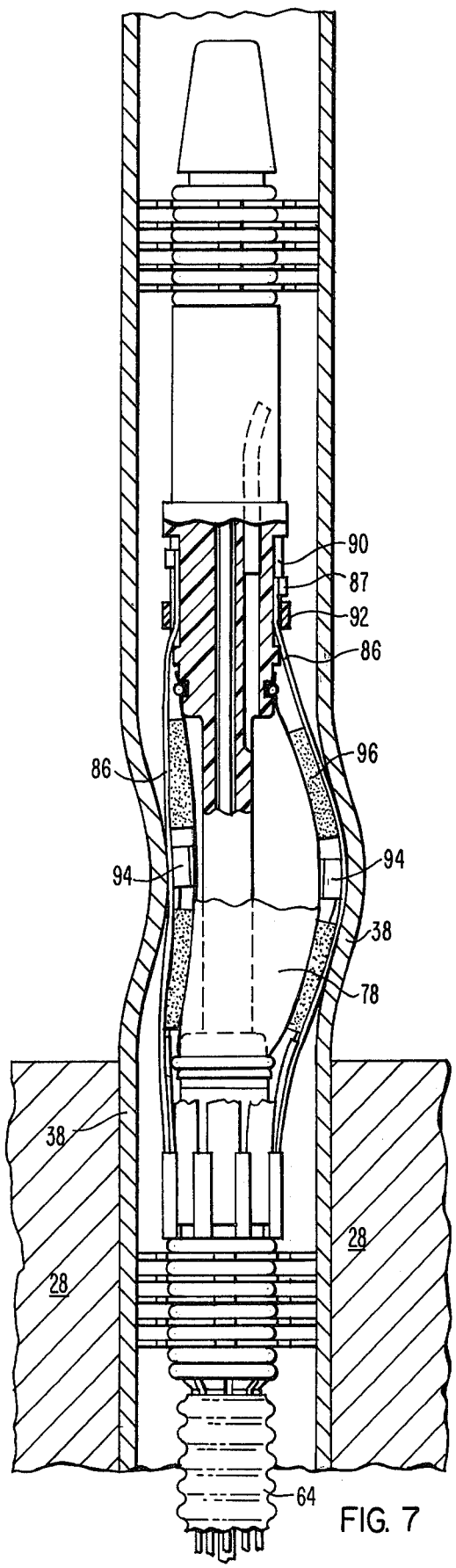

INFLATABLE EDDY CURRENT INSPECTION PROBE FOR INSPECTION OF TUBULAR MEANS

CROSS-REFERENCE TO RELATED APPLICATIONS

The invention described herein is related to copending application Ser. No. 903,377, filed May 5, 1978, entitled "Internal Diameter Measuring Apparatus" and U.S. patent application Ser. No. 936,297, filed Aug. 23, 1978, entitled "Probe Positioner", both of which are assigned to the assignee of the present application.

BACKGROUND OF THE INVENTION

This invention relates to inspection apparatus, and more particularly, to inspection probes for inspecting tubular members.

There are many situations in which a hazardous environment limits human access to various locations. One such situation occurs in the inspection and repair of nuclear steam generators. A typical nuclear steam generator comprises a vertically oriented shell, a plurality of U-shaped tubes disposed in the shell so as to form a tube bundle, a tube sheet for supporting the tubes at the ends opposite the U-like curvature, and a dividing plate that cooperates with the tube sheet, forming a primary fluid inlet plenum at one end of the tube bundle and a primary fluid outlet plenum at the other end of the tube bundle. The primary fluid, having been heated by circulation through the nuclear reactor core, enters the steam generator through the primary fluid inlet plenum. From the primary fluid inlet plenum, the primary fluid flows upwardly through first openings in the U-tubes near the tube sheet which supports the tubes, through the U-tube curvature, downwardly through second openings in the U-tubes near the tube sheet, and into the primary fluid outlet plenum. At the same time, a secondary fluid, known as feedwater, is circulated around the U-tubes in heat transfer relationship therewith, thereby transferring heat from the primary fluid in the tubes to the secondary fluid surrounding the tubes, causing a portion of the secondary fluid to be converted to steam. Since the primary fluid contains radioactive particles and is isolated from the secondary fluid by the U-tube walls and tube sheet, it is important that the U-tubes and the tube sheet be maintained defect-free so that no breaks will occur in the U-tubes or in the welds between the U-tubes and the tube sheet, thus preventing contamination of the secondary fluid by the primary fluid.

Occasionally, it is necessary to either inspect or repair the U-tubes or the tube sheet welds by way of access through the primary fluid inlet and outlet plena. For this purpose, manways are provided in the vertical shell so that working personnel may enter the inlet and outlet plena to perform operations on the U-tubes and tube sheet. However, since the primary fluid, which is generally water, contains radioactive particles, the inlet and outlet plena become radioactive, which thereby limits the time that working personnel may be present therein. Accordingly, it would be advantageous to be able to perform operations on the U-tubes and tube sheet without requiring the presence of working personnel. There are several mechanisms known in the art that attempt to provide a solution to this problem; but none of them has been able to completely solve the problem.

A particular probe known in the art for inspection tubes has a single eddy current coil mounted on a mechanical support which constitutes the probe. The eddy current coil is mounted on a spring-loaded piston which has its axis on a radius of the probe so that the coil is pushed outwardly into contact with the internal surface of the tube and can follow the contour of the inner surface of the tube to be inspected. Since a single eddy current coil can detect a crack in only a 45° sector of the tube wall, the single coil must be rotated to scan the entire surface of the tube wall. Since it is necessary to rotate this particular probe in order to inspect the entire tube at any particular cross-section, it has been found that rotation of the probe causes the coil to impact certain irregularities on the internal surface of the tube, which causes the eddy current coil to become damaged. Therefore, what is needed is a probe that is capable of remotely inspecting the internal surface of a tube in a nuclear steam generator without having to be rotated and that is capable of repeated use without being damaged.

SUMMARY OF THE INVENTION

The inspection probe comprises a central body attached to a hollow nylon tube with an inflatable rubber tube mounted around a portion of the central body. A plurality of plastic strips, which may number eight, are axially disposed on the central body with one end of each of the plastic strips being firmly attached to the central body, and with the other end of the plastic strips being slidably attached to the central body. Each plastic strip has an eddy current coil mounted thereon that is capable of detecting cracks in the surfaces of tubular members. When the rubber tube has been inflated, it causes the plastic strips with the eddy current coils mounted thereon to be pressed into close contact with the internal surface of the tubes so that the eddy current coils may inspect that surface. The plastic strips and rubber tube are sufficiently pliable so as to be able to conform to irregular surface configurations of the tubes.

BRIEF DESCRIPTION OF THE DRAWINGS

While the specification concludes with claims particularly pointing out and distinctly claiming the subject matter of the invention, it is believed the invention will be better understood from the following description taken in conjunction with the accompanying drawings, wherein:

FIG. 6 is an elevational view in cross-section of the probe disposed within a tube; and FIG. 7 is a cross-sectional view in elevation of the probe disposed within a deformed tube.

DESCRIPTION OF THE PREFERRED EMBODIMENT

In a tube-type steam generator, a tube sheet supports a bundle of heat transfer tubes. The invention described herein provides a probe that is capable of remotely inspecting the heat transfer tubes in a nuclear steam generator.

Figure 1:
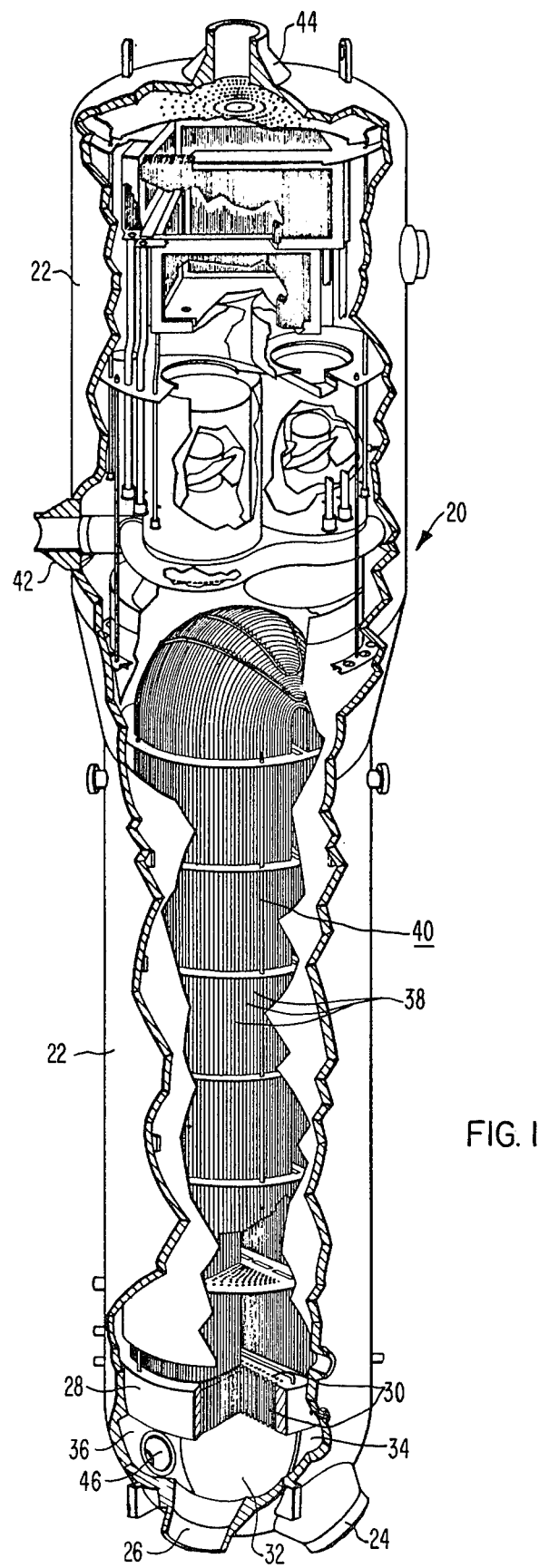
FIG. 1 is a partial cross-sectional view in elevation of a typical steam generator.

Referring to FIG. 1, a nuclear steam generator referred to generally as 20, comprises an outer shell 22 with a primary fluid inlet nozzle 24 and a primary fluid outlet nozzle 26 attached thereto near its lower end. A generally cylindrical tube sheet 28, having tube holes 30 therein, is also attached to outer shell 22 near its lower end. A dividing plate 32 attached to both tube sheet 28 and outer shell 22 defines a primary fluid inlet plenum 34 and a primary fluid outlet plenum 36 in the lower end of the steam generator, as is well understood in the art. Tubes 38 which are heat transfer tubes shaped with a U-like curvature are disposed within outer shell 22 and attached to tube sheet 28 by means of tube holes 30. Tubes 38, which may number about 7,000, form a tube bundle 40. In addition, a secondary fluid inlet nozzle 42 is disposed on outer shell 22 for providing a secondary fluid, such as water, while a steam outlet nozzle 44 is attached to the top of outer shell 22. In operation, the primary fluid which may be water having been heated by circulation through the nuclear reactor core enters steam generator 20 through primary fluid inlet nozzle 24 and flows into primary fluid inlet plenum 34. From primary fluid inlet plenum 34, primary fluid flows upwardly through tubes 38, through tube sheet 28, up through the U-shaped curvatures of tubes 38, down through tubes 38 and into primary fluid outlet plenum 36, where the primary fluid exits the steam generator through primary fluid outlet nozzle 26. While flowing through tubes 38, heat is transferred from the primary fluid to the secondary fluid which surrounds tubes 38, causing the secondary fluid to vaporize. The resulting steam then exits the steam generator through steam outlet nozzle 44. On occasion, it is necessary to inspect or repair tubes 38 or the welds between tubes 38 and tube sheet 28 to assure that the primary fluid, which may contain radioactive particles, remains isolated from the secondary fluid. Therefore, manways 46 are provided in outer shell 22 to provide access to both primary fluid inlet plenum 34 and primary fluid outlet plenum 36 so that access may be had to the entire tube sheet 28.

Referring to FIGS. 2-5, the inspection probe is referred to generally as 50 and comprises a nose 52, a central body 54, and a tail 56. Nose 52, central body 54, and tail 56 may be constructed of nylon and are firmly attached together so as to form the structural body of the inspection probe 50. A bore 58 extends the entire length of probe 50 and had disposed therein a stainless steel flexible cable 60, which is brazed to a rivet 62 in nose 52 so as to hold cable 60 within probe 50. Cable 60 guarantees that probe 50 can be pulled out of a particular tube even if probe 50 becomes firmly lodged in a particularly dented location. Bellows tubing 64, which may be chosen from flexible tubing well known in the art, is connected to tail 56 and acts as a springy flexible connector between probe 50 and a long section of stiff nylon tubing 66. Nylon tubing 66 forms the push rod for probe 50 and carries the electrical leads from the probe to instrumentation located outside the steam generator 20. Since the nylon tubing 66 is fairly stiff, it may be used to remotely insert or withdraw the probe 50 from any tube 38 of the nuclear steam generator 20. In copending application Ser. No. 936,297, filed Aug. 23, 1978, entitled "Probe Positioner", there is described a device for remotely positioning an inspection probe of the type such as probe 50.

Figure 5:
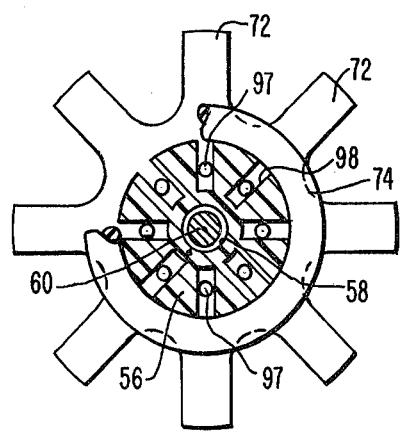
FIG. 5 is a view along line V—V of FIG. 2.

Still referring to FIGS. 2-5, a first positioning mechanism 68 is mounted on nose 52, while a second positioning mechanism 70 is mounted on tail 56 so as to provide a means by which probe 50 is always centrally located within a particular tube 38. First positioning mechanism 68 and second positioning mechanism 70 may comprise brushes 72, which may be 0.005 inch thick polyester sheets shaped in the form as shown in FIG. 5, together with rubber O-rings 74. O-rings 74 are stretched over nose 52 and tail 56, while brushes 72 are disposed between a set of O-rings 74. O-rings 74 provide a means by which brushes 72 may be attached to probe 50. Brushes 72 have the capability of being able to be passed through a constricted portion of a tube 38, while also being capable of contacting the inside surfaces of a tube 38 at a section of the tube that has no constrictions. Therefore, it can be seen that first positioning mechanism 68 and second positioning mechanism 70 provide a means by which probe 50 may traverse constricted portions of a tube 38 while still maintaining central alignment within such a tube.

Figure 2:
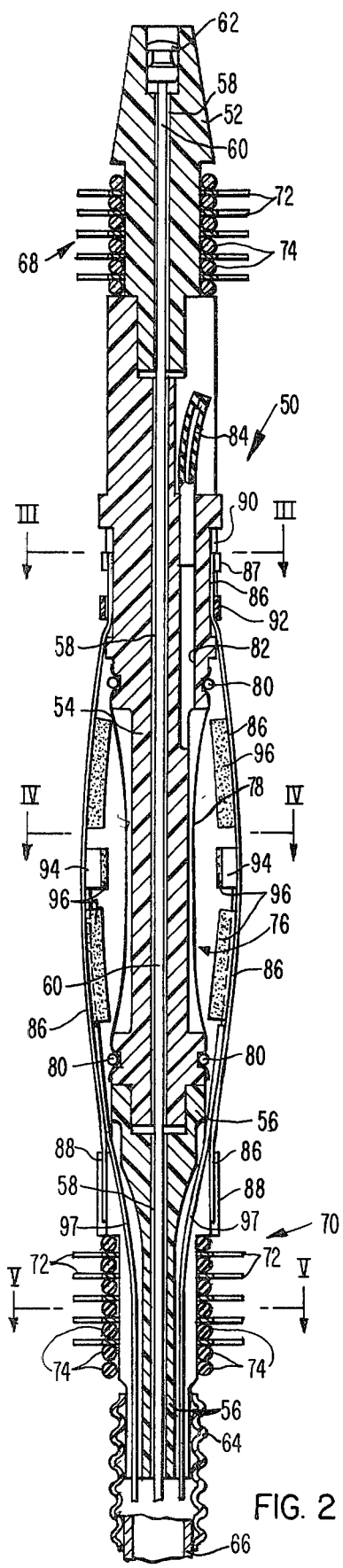
FIG. 2 is a cross-sectional view in elevation of the probe.
Figure 4:
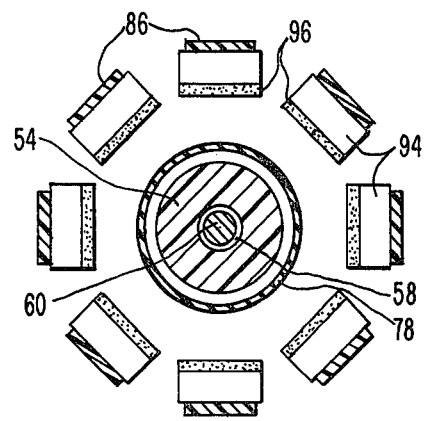
FIG. 4 is a view along line IV—IV of FIG. 2.
Figure 3:
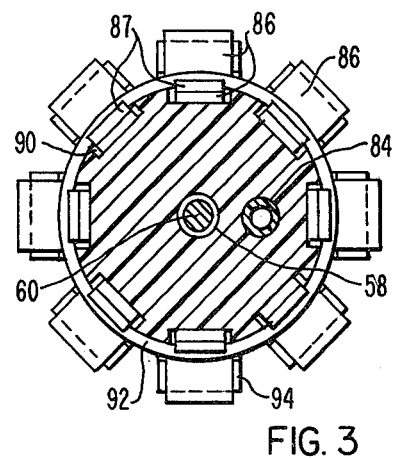
FIG. 3 is a view along line III—III of FIG. 2.

An inflation mechanism 76 is disposed over central body 54, as shown in FIG. 2. Inflation mechanism 76 may comprise a cylindrical rubber tube 78, which may be approximately 0.007 inches thick and mounted around the section of central body 54 that has a reduced diameter, as shown in FIG. 2. Rubber tube 78 is sealed to central body 54 at its top and bottom ends by second O-rings 80. Central body 54 also has a channel 82 therein that extends from the outside of central body 54 to within the annulus defined by rubber tube 78 and the reduced diameter section of central body 54. A vinyl tube 84 is attached to the outer end of channel 82 so that a hyperdermic syringe may be inserted into the outer end of vinyl tube 84 for pressurizing inflation mechanism 76. Pressurizing inflation mechanism 76 by means of introducing a gas such as air through vinyl tube 84, through channel 82, and into the annular section defined by central body 54 and rubber tube 78 causes rubber tube 78 to be expanded outwardly as shown in FIGS. 6 and 7. Once rubber tube 78 has been expanded, vinyl tube 84 may be heat sealed, and the hyperdermic syringe removed to prevent air leakage from vinyl tube 84, thus preserving the inflation of rubber tube 78. The air pressure maintained within rubber tube 78 may be approximately 2 psi.

Uniformly spaced around central body 54 are a plurality of flat strips 86. The strips may number approximately eight and have a thickness of approximately 0.01 inches. Strips 86 may be constructed from a fairly rigid but pliable plastic, such as Polyester. At one end strips 86 are cemented into slots 88 in tail 56 of probe 50. At the other end, strips 86 have a stop 87 attached to its outer surface and are free to move in grooves 90. Strips 86 are prevented from being pulled out of grooves 90 by stops 87 contacting a band of heat shrinkable tubing 92. While the heat shrinkable tubing 92 and stops 87 prevent the end of strips 86 from being totally dislodged from grooves 90, the heat shrinkable tubing 92 does not inhibit the sliding of strips 86 in grooves 90.

An eddy current coil 94, which may be chosen from those well known in the art, is cemented to the inner surface of each of the strips 86 by means of Eastman 910 cement. Although the drawings show all eight eddy current coils 94 in a common radial plane, the eddy current coils 94 may be disposed in two radial planes, with four coils in each plane. In addition, pads 96 of foam rubber are cemented to the inner side of each strip 96 above and below each eddy current coil. Pads 96 may also be attached to the back of each eddy current coil 94. Pads 96 serve to keep the surface of rubber tube 78 well below the strips 86 so that the rubber tube 78 does not expand out between the strips 86 and rub against the tube wall, thereby preventing the rubber tube from being punctured. The electrical leads 97 from eddy current coils 94 are brought through radial slots 98 in tail 56 of probe 50 so that the electrical leads may pass through brushes 72 to the space inside bellows tubing 64. Electrical leads 97 continue through bellows tubing 64 and through nylon tubing 66 to instrumentation located outside steam generator 20 which may be chosen from those well known in the eddy current inspection art.

OPERATION

Once rubber tube 78 has been inflated, as previously described, probe 50 may be inserted into a particular tube 38, either manually or remotely, as shown in FIG. 6. As shown in FIG. 6, inflation mechanism 76 is in an inflated condition such that should probe 50 encounter a constriction or other irregularity in the tube wall, inflation mechanism 76 will conform to the shape of the inside surface of the tube 38. Since the inspection process is performed while probe 50 is being withdrawn at a rate of approximately one foot per second, the eddy current coils must be capable of rapid radial movement so that the coils can follow the contour of the tube 38. The pressurized air within rubber tube 78 provides such a rapid response so that strips 86 with eddy current coils 94 attached thereto are in continual contact with the interior surface of the tube 38.

Referring now to FIG. 7, when inflation mechanism 76 encounters a dented situation, inflation mechanism 76 assumes the form shown in FIG. 7 on the indented side thereof. On the other hand, when inflation mechanism 76 encounters a bulged area in the tube 38, inflation mechanism 76 assumes the shape as shown in the bulged portion of FIG. 7. Inflation mechanism 76 is capable of inspecting both a dented and a bulged section of a tube, including a section of a tube that contains both a dent and a bulge at the same cross-section, as shown in FIG. 7. As probe 50 is pulled through the tube 38, brushes 72 maintain alignment of probe 50 within tube 38, as shown in FIG. 7. When the probe 50 encounters an irregularity in tube 38, the instrumentation located outside of the steam generator 20 records the readings of each eddy current coil 94. As is well understood in the eddy current art, should any eddy current coil encounter a crack or other singularity in the tube 38, a corresponding reading on the instrumentation located outside the steam generator 20 would be apparent to an operator thereof. Such a reading would indicate that the chosen tube 38 has a defect therein. Therefore, the invention provides an inspection probe that is capable of remotely inspecting a tube in a nuclear steam generator.

What is claimed is:

1. An inspection probe for internally inspecting tubes comprising:
   a central body capable of being disposed in said tube;
   a plurality of flexible strips having one end firmly attached to said central body and having the other end slidably attached to said central body;
   an eddy current coil attached to each of said strips;
   inflatable means disposed on said central body and between said central body and said strips for expanding said strips into contact with said tube, thereby placing said eddy current coil in close proximity to said tube for detecting defects in said tube;
   pads mounted on the inner side of said strips for preventing said inflation means from being damaged by said tube;
   a nose attached to said central body and having at least two elastomeric members disposed therearound with a brush disposed therebetween and with said brush being capable of extending into contact with said tube for positioning said probe within said tube; and
   a tail attached to said central body and having at least two elastomeric members disposed therearound with a brush disposed therebetween and with said brush being capable of extending into contact with said tube for positioning said probe within said tube.

2. The inspection probe according to claim 1 wherein said inflatable means comprises a rubber tube disposed over said central body and attached thereto.

3. The inspection probe according to claim 2 wherein said probe further comprises:
   a flexible cable extending through said nose, said central body, and said tail for insuring that said probe can be pulled from said tube.

4. The inspection probe according to claim 3 wherein said probe further comprises bellows tubing attached to said tail for providing flexibility to said probe.

5. The inspection probe according to claim 4 wherein said probe further comprises hollow nylon tubing attached to said bellows tubing for positioning said probe and for carrying electrical leads from said eddy current coils to recording instrumentation.

6. The inspection probe according to claim 5 wherein said strips are flexible plastic strips.

* * * * *